United States Patent [19]

Striese

[11] 4,350,165
[45] Sep. 21, 1982

[54] MEDICAL ELECTRODE ASSEMBLY

[75] Inventor: Jim G. Striese, Brockton, Mass.

[73] Assignee: TRW Inc., Cleveland, Ohio

[21] Appl. No.: 152,945

[22] Filed: May 23, 1980

[51] Int. Cl.³ .............................................. A61B 5/04
[52] U.S. Cl. .................................. 128/640; 128/641
[58] Field of Search ............................ 128/639–641, 128/644, 783, 798, 802, 803

[56] References Cited

U.S. PATENT DOCUMENTS

| 3,865,099 | 2/1975 | Robichoud | 128/641 |
| 4,019,500 | 4/1977 | Patrick, Jr. et al. | 128/641 |
| 4,166,453 | 9/1979 | McClelland | 128/639 |
| 4,166,456 | 9/1979 | Wilson | 128/640 |
| 4,270,544 | 6/1981 | Gilden | 128/640 |

*Primary Examiner*—Lee S. Cohen

*Attorney, Agent, or Firm*—James R. O'Connor; Thomas C. O'Konski; John F. McKenna

[57] ABSTRACT

A disposable medical electrode includes a compliant annular support layer having an adhesive surface, a compliant discoid gel pad having a diameter less than the inner diameter of the support layer, an electrical terminal and a holder for maintaining the support layer, gel pad and terminal in relative juxtaposition. The holder includes a pair of mating sections which can be clamped together on opposite sides of the support layer and terminal to retain those components against relative motion. Also, one section includes a central passage through it for snugly receiving the gel pad so that one surface of the gel pad is in intimate contact with the terminal and the opposite surface of the gel pad is exposed at the outer end of said passage and lies more or less in the same plane as the adhesive surface of the support layer.

15 Claims, 6 Drawing Figures

MEDICAL ELECTRODE ASSEMBLY

This invention relates generally to the field of medical electrodes, and more particularly, to an improved holder assembly for such an electrode.

BACKGROUND OF THE INVENTION

It has been known for some time that certain parts of the human body, for example the brain and the heart, generate, or respond to, identifiable electrical signals. Furthermore, nerve impulses in general are known to have electrical components that can be detected using appropriate medical electrodes. The study of these signals can be useful in the diagnosis or monitoring of certain conditions and diseases. Generally, these signals are of relatively low strength, and associated with relatively high levels of noise. Consequently, the medical electrodes used to sense them must have relatively high levels of sensitivity. This usually requires that the electrodes be placed directly on the skin so as to make very good electrical contact with the skin surface, and be resistant to the influence of external forces such as those resulting from patient movement.

In many diagnostic or monitoring procedures, the electrodes are worn by the patient for relatively long periods of time. Thus, in addition to being sensitive, the electrodes must also be reasonably comfortable to wear. They cannot cause undue skin irritation, which can affect the results of the monitoring or cause patient discomfort.

It has become commonplace now to use disposable medical electrodes, both for sanitary reasons and to reduce the time and labor that is normally involved in cleaning nondisposable electrodes that may have been used previously. With disposable electrodes, it is important to minimize the cost of the electrodes and still provide the required sensitivity and comfort.

Typical prior art disposable medical electrodes include three basic components: a support layer of compliant material having an adhesive undersurface to permit attachment to the skin; an electrical terminal for attachment to an electrical lead that carries the sensed signals to the monitoring or diagnostic equipment; and, a pad filled with a conductive gel that contacts the skin and provides a good electrical connection between the skin and the terminal. Various techniques have been used to combine these three electrode components into a single unit. For example, in the electrodes disclosed in U.S. Pat. Nos. 3,828,766; 3,901,218; 3,989,035; 4,019,500; 4,063,352; and 4,067,322, the electrical terminal is composed of two parts, typically an eyelet and mating stud, which are pressfit together to form the terminal. The adhesive support layer, or another layer attached to the support layer, is positioned between the stud and eyelet so that when the stud is pressed into the eyelet, the layer is caught therebetween and held in place.

The primary problem with such two-part terminals is their cost. Since both parts of the terminal must be electrically conductive, they both must be made of, or at least coated or plated with, a non-corrosive, electrically conductive material such as silver or silver chloride. Because of this, the electrically conductive terminal parts are generally the most expensive parts of the electrode. Further, with electrodes of this type, the third component, the gel pad, is either not secured to the support layer or terminal, giving rise to motion artifacts in the output signal, or is secured through the use of welding or an adhesive, adding to the cost of manufacturing the electrode.

To avoid the high cost of two-part terminals, various disposable medical electrodes have been proposed that utilize a single-part terminal. Such single-part-terminal electrodes can be divided into two general types. One type, illustrated in U.S. Pat. Nos. 3,868,946; 4,029,086; and 4,066,078, retain the support layer, terminal and gel pad relative to one another by means of adhesive which, as noted above, adds to the cost of manufacturing the electrodes. Electrodes of the other type shown in U.S. Pat. Nos. 3,752,151; 3,865,099; and 3,882,853, utilize rather complicated single piece holding members. In these constructions, the terminal, the support layer or both are actually welded to the holder adding to the cost. Also, the gel pad is either left unsecured, or secured through the use of an adhesive, giving rise to the same disadvantages discussed above.

SUMMARY OF THE INVENTION

The present invention broadly aims to provide a new and improved medical electrode.

A more specific object of the invention is to provide a disposable medical electrode that includes improved means for stably supporting the basic components of the electrode relative to one another.

Another object of the invention is to provide a disposable medical electrode of the type described that, because of its stability, minimizes sensed signal variations due to the influence of external forces, such as patient movement.

Another object of the invention is to provide a disposable medical electrode of the type described that is relatively low in cost and simple to manufacture and assemble.

Still another object of the invention is to provide a disposable medical electrode of the type described that is comfortable to wear.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

In general, the medical electrode of this invention includes an electrically conductive terminal which may be in the form of a male snap fastener element made entirely of metal or of plastic with a conductive coating. Intimately associated with the undersurface of the terminal is a gel pad which is filled with a conductive electrolyte. In use, the terminal and the gel pad are supported against the patient's skin by a thin annular support layer made of compliant material, the undersurface of which carries an adhesive coating.

Instead of combining or assembling these three basic components by means of adhesives or integrating them into a fixture by welding, they are captured between a pair of thin, nonconductive holder sections which snap together against the top and bottom surfaces of the support layer at the inner edge margin thereof. The cooperating holder sections maintain the relative positions of the terminal, the gel pad and the support layer to establish intimate electrical contact between the terminal and the gel pad and to prevent relative movement between the electrode components which may give rise to motion artifacts in the monitor signal initiated by the electrode.

The holder sections are simple, inexpensive, plastic parts which can be molded or otherwise formed in quantity extremely inexpensively. Indeed, their cost can be less than the cost of the usual conductive stud present in the two-piece terminal-type medical electrodes. However, the present electrode construction results in additional cost savings by virtue of the fact that the various components of the electrode can be assembled very quickly and easily simply by juxtaposing those components and fastening together the two holder sections.

When so assembled, the medical electrode is a very compact, light-weight compliant article which, when affixed to a patient, should cause minimum patient discomfort. Yet it should pick up monitor signals with the required high sensitivity and low noise level to yield meaningful information about the patient function being monitored.

BRIEF DESCRIPTION OF THE DRAWINGS

For a fuller understanding of the nature and objects of the invention, reference should be had to the following detailed description, taken in connection with the accompanying drawings, in which.

DESCRIPTION OF THE PREFERRED EMBODIMENTS

Figure 1:
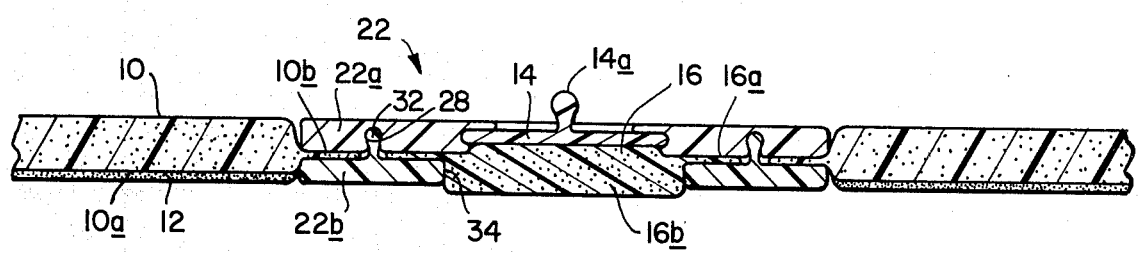
FIG. 1 is a fragmentary view in transverse section of a medical electrode embodying the principles of this invention.
Figure 2:
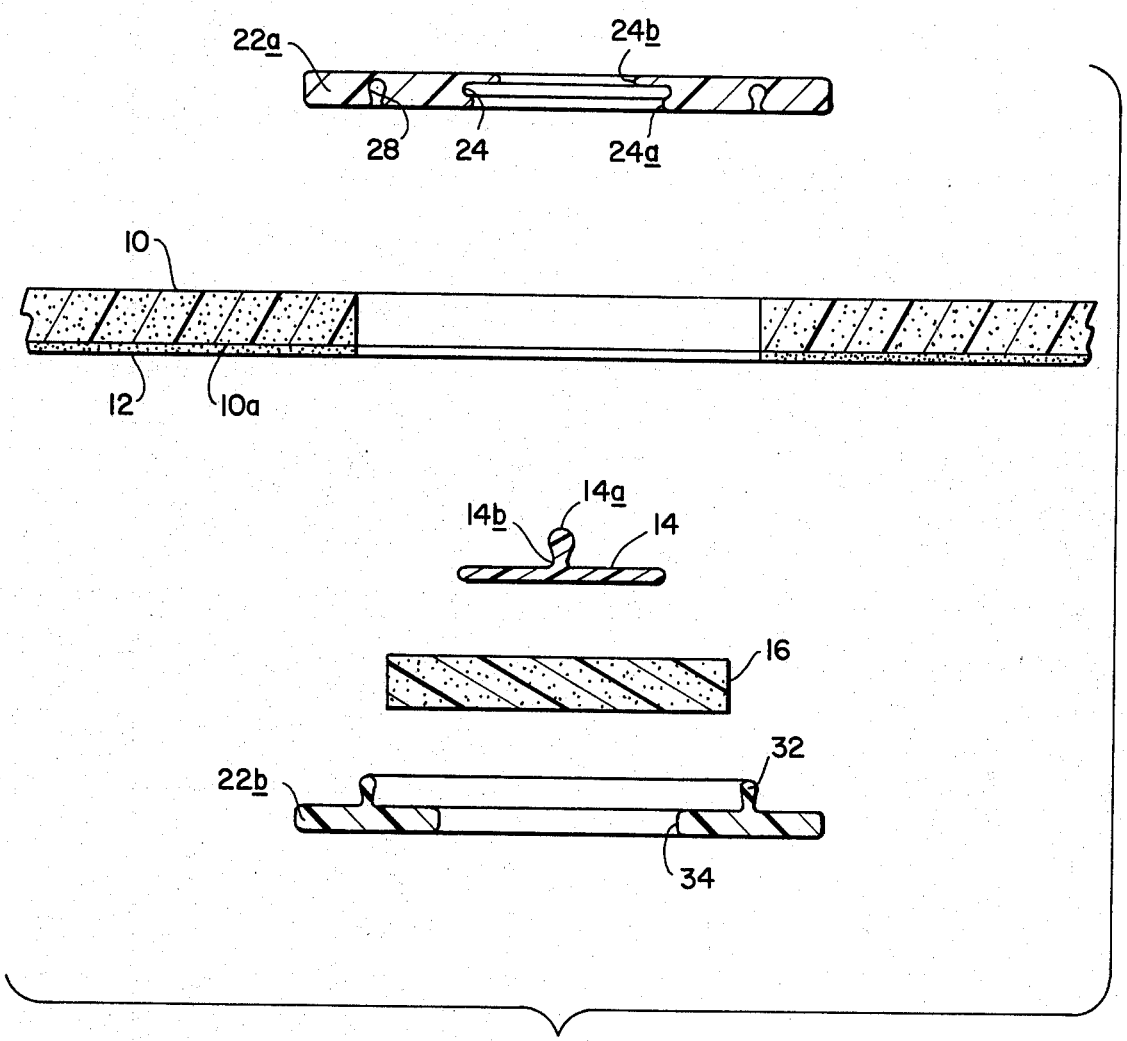
FIG. 2 is an exploded view showing the various components of the FIG. 1 electrode in transverse section.

Referring to FIGS. 1 and 2 of the drawings, an electrode made in accordance with this invention includes a flat annular support layer 10 made of a suitable compliant material such as closed-cell foam plastic. The undersurface 10a of the support layer carries an adhesive coating 12 for adhering the support layer to the skin of a patient.

The electrode also includes a conductive terminal 14 which in the illustrated embodiment is in the form of a male snap fastener element having the usual protruding bulbous top 14a and narrow neck 14b. The electrode top is arranged to be removably connected to a mating female fastener element electrically connected to monitoring equipment. The terminal 14 may be made of a conductive metal. Alternatively, to lower its cost, it may be made of a plastic material such as glass impregnated ABS plastic and plated or otherwise coated with a conductive material such as silver metal or a silver-silver-chloride composition.

The electrode also includes the usual wafer-like gel pad 16 made of open cell foam plastic, which, in use, is impregnated with a conductive electrolyte such as Redux Creme or Ferris Gel. The aforesaid three primary components of the electrode are all maintained in juxtaposition by a holder made of a suitable plastic material such as polystyrene and shown generally at 22 in FIG. 1.

Still referring to FIGS. 1 and 2, the holder 22 comprises a flat annular upper section 22a and a flat annular lower section 22b, both sections having the same diameter, which diameter is somewhat greater than the inner diameter of the annular support layer 10. Formed in the underside of section 22a is a circular recess 24 which is centered on the circular axis of that section. Recess 24 extends almost all the way to the top of section 22a. Formed near the mouth of that recess is a small radially inwardly extending flange or lip 24a. The diameters of the recess 24 and its lip 24a are such that the circular body of the terminal 14 can be snapped into that recess and be securely retained there by the lip 24a with the terminal top 14a projecting out through a central opening 24b in the top of holder section 22a.

Also formed in the underside of section 22a radially outboard of the recess 24 is a circular slot 28 which cooperates with a mating part on the holder section 22b to connect those two sections together as will be described presently.

The holder section 22b is simply a flat annular part which is formed with a raised circular rib 32 whose diameter corresponds to that of the slot 28 in section 22a. Preferably, the cross-sectional shapes of the rib 32 and slot 28 are necked down as illustrated so that the rib 32 can be snapped into the slot 28 and be securely retained there.

To assemble the electrode, the terminal 14 is snapped into place in the recess 24 in section 22a. Then the support layer 10 is positioned on section 22b outboard of the circular rib 32. Likewise, the circular gel pad 16 is positioned on section 22b inboard of that rib. Obviously then, the diameter of the rib 32 is correlated with the diameter of pad 16 and the inner diameter of support layer 10 to permit the aforesaid positioning of those elements. Thus the holder section 22b constitutes a jig or fixture for assuring the proper positioning of the support layer and gel pad relative to one another.

Finally, the holder section 22a is superimposed on section 22b and the two sections are pressed together so that the rib 32 snaps into the slot 28 thereby clamping the two holder sections together on opposite sides of the support layer 10. Thus the holder not only captures the inner edge margin 10b of that support layer, but also the outer edge margin 16a of the gel pad, compressing those edge margins as needed to permit the sections to clamp together. The unclamped inner portion 16b of the gel pad projects out through the central opening 34 in the bottom holder section 22b where its exposed surface projects slightly beyond the undersurface of holder section 22b and the adhesive coated support layer surface 10a. Obviously, then, for best results, the combined thickness of the clamped-together sections 22a and 22b should approximate the thickness of layer 10.

When the two holder sections are clamped together as described and illustrated, they firmly maintain the support layer 10, the terminal 14 and the gel pad 16 in the proper juxtaposition to assure intimate electrical contact between the gel pad and the terminal 14 base. Consequently, when the support layer is adhered to the patient's skin, stable intimate electrical contact will exist between the skin and the terminal so that the electrical monitor signals picked up by the electrode will exhibit maximum sensitivity with minimum noise.

The gel pad 16 is normally impregnated with electrolyte after assembly. Then a strippable cover strip is adhered to the adhesive side of the support layer to protect the adhesive coating 12 thereon and also to encapsulate the gel pad to ensure the electrolyte therein does not dry out and lose its electrical conductivity during the shelf life of the electrode.

Figure 3:
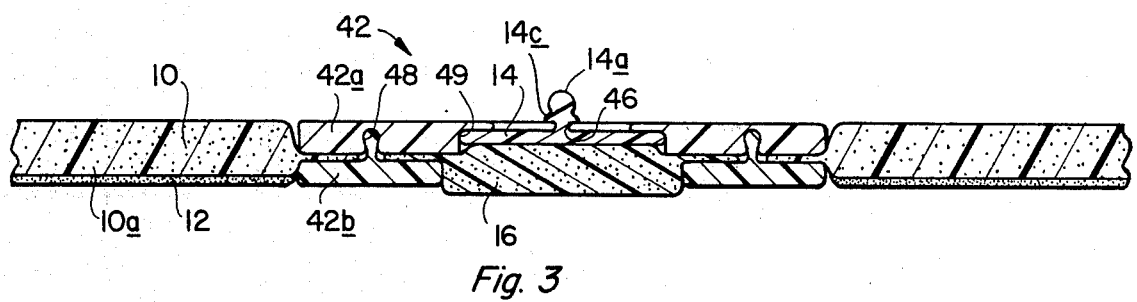
FIG. 3 is a view similar to FIG. 1 of a second electrode embodiment.
Figure 4:
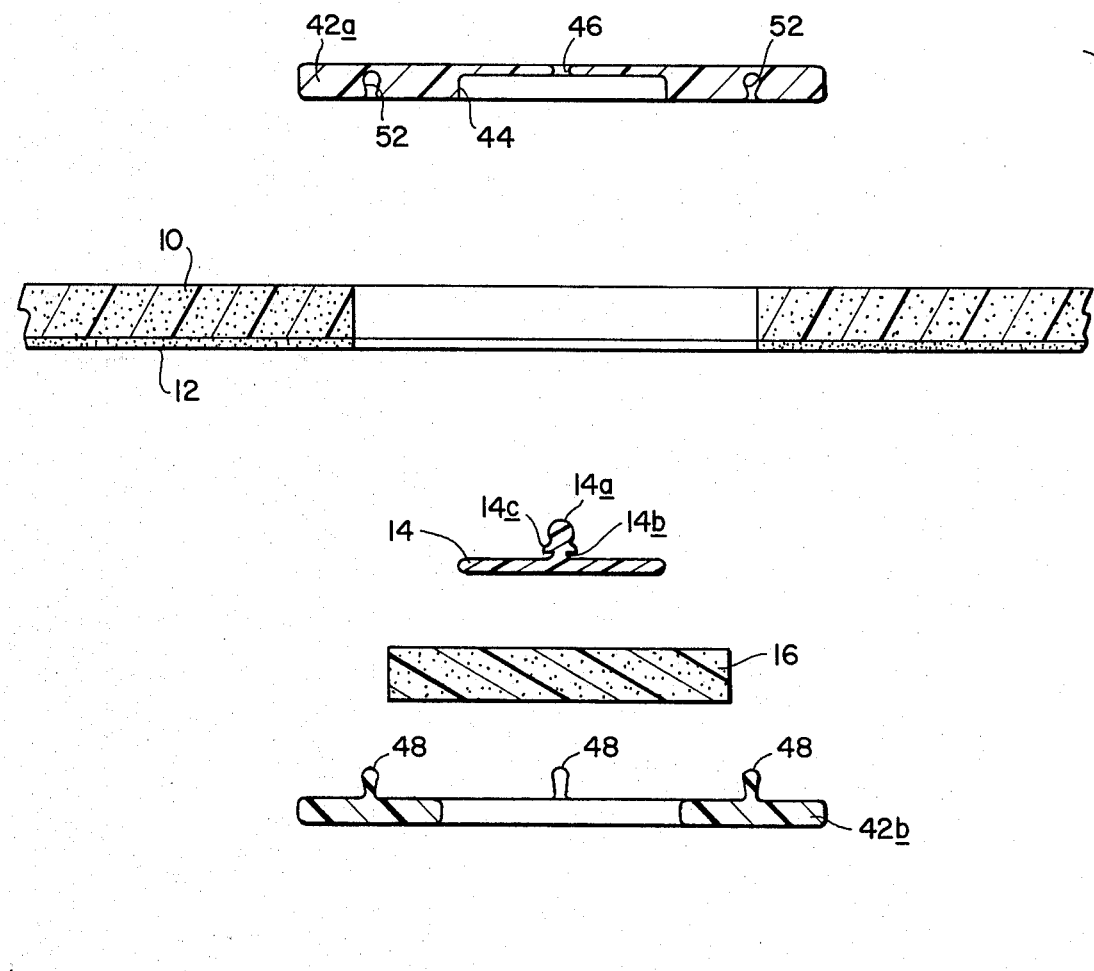
FIG. 4 is a view similar to FIG. 2 showing the components of the second electrode embodiments in greater detail.

FIGS. 3 and 4 of the drawings illustrate a slightly different electrode embodiment. For the most part, the components thereof are similar to those found in the FIG. 1 electrode. Accordingly, the common components carry the same identifying numerals. This electrode version employs a holder shown generally at 42 comprising an upper section 42a and a lower section 42b. In this case, however, the upper section is substantially discoid and is provided with a generally cylindrical recess 44 in its underside for receiving the terminal 14. In this embodiment, the terminal 14 is retained in place within section 42a by the engagement of the terminal top 14b through a small opening 46 in the top of section 42a. Preferably, in order to maintain firm connection between the terminal and the holder section, the terminal top 14a is provided with an annular collar or protuberance 14c around neck 14b which snaps through opening 46.

The holder 42 differs from holder 22 also in that, instead of the two holder sections being connected together by a mating collar and slot, section 42b is formed with a circular array of raised bulbous stems 48 which are arranged to snap into a corresponding array of cavities 52 formed in the underside of the holder section 42a. Thus the two holder sections snap together much like a common snap fastener.

The FIG. 3 electrode embodiment is assembled in more or less the same way as the FIG. 1 embodiment and it possesses the same advantages. First the terminal is snapped in place in its recess 44. Then the support layer 10 and gel pad 16 are located on the lower holder section 42b without and within the stems 48 respectively. Finally, the top holder section is snapped onto the bottom section, thereby capturing the support layer and gel pad in between.

Figure 5:
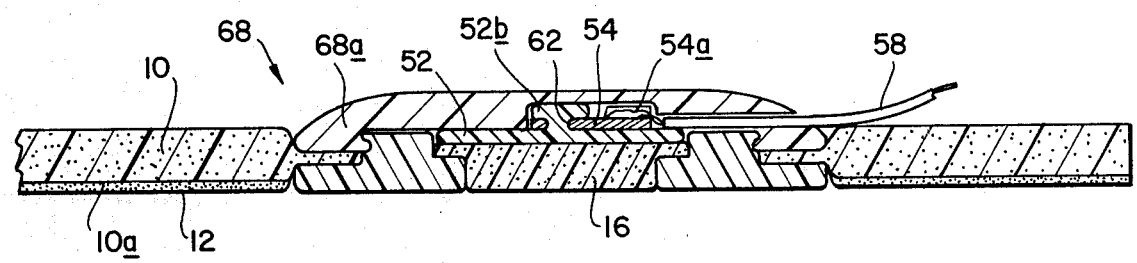
FIG. 5 is a view similar to FIG. 1 of still another embodiment of my electrode.
Figure 6:
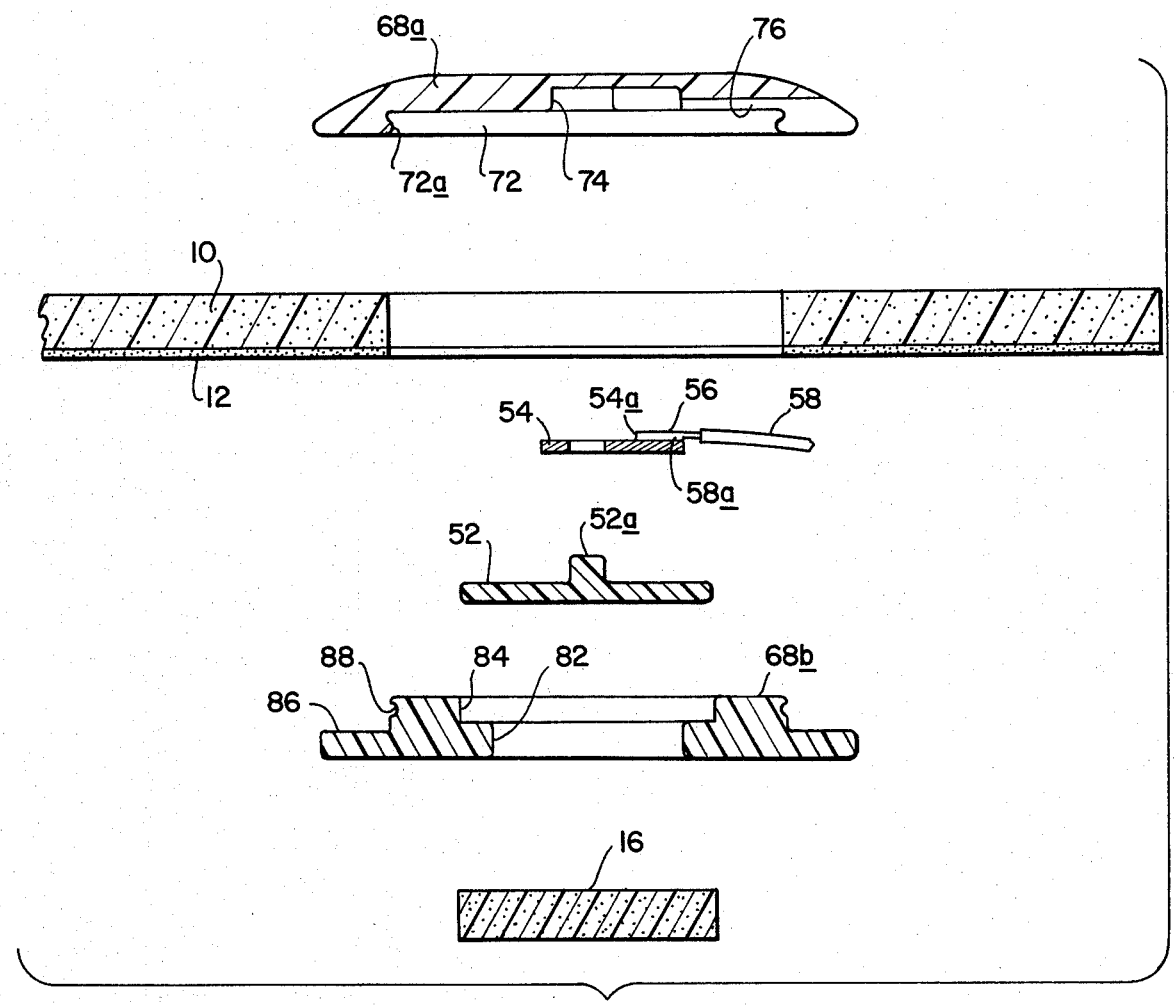
FIG. 6 is an exploded view showing the parts of the FIG. 5 electrode in transverse section.

FIGS. 5 and 6 show still another embodiment of my improved medical electrode. Instead of having a detachable snap fastener-type terminal, the FIG. 5 electrode employs a terminal which is permanently attached to its electrical lead. The terminal is composed of two parts, namely a discoid contact member 52 formed with a centrally located upstanding boss 52a. The contact member may be solid metal or comprise a plastic body covered with a conductive coating similar to terminal 14 described above. Mounted to the top of contact member 52 is a conductive terminal strip 54 made of a suitable noncorrosive metal such as brass. The terminal strip 54 may be circular with a diameter somewhat smaller than that of contact member 52 or it may be a simple rectangular structure. In any event, it is formed with a raised boss 54a containing a lateral passage 56. Extending into passage 56 is the stripped end 58a of an insulated electric lead 58. After insertion of the lead end 58a into passage 56, the boss 54a is crimped to permanently attach the lead to the terminal strip.

Terminal strip 54 also contains a vertical opening 62 which is sized to receive the contact member boss 52a. After the terminal strip is seated on the contact member, the boss 52a is upset over the strip as shown at 52b in FIG. 1 by a staking operation to permanently attach the terminal strip to the contact member.

The FIG. 5 electrode embodiment also differs from the others in the make-up of its holder shown generally at 68. More particularly, the holder includes a first or upper holder section 68a in the form of a flat discoid member made of a suitable impact-resistant, electrically-insulating plastic material such as plystyrene. It has a rounded top surface devoid of sharp edges. Formed in its undersurface is a relatively large circular recess 72 having a radially inwardly extending lip 72a at its entrance. Also a well 74 is present at the bottom of that recess for accommodating the terminal strip 54 as will be described later. Moreover, a lateral slot 76 is formed in the underside of section 68a which slot extends from well 74 out through the side wall of section 68a to provide a feedthrough for the electrical lead 58.

The lower holder section 68b made of the same material as section 68a has the shape of a flat annulus with the opening 82 through that section having a relatively large diameter. Formed in the upper surface of section 68b is a circular recess 84 having a diameter somewhat larger than that of opening 82. Otherwise, that upper surface is flat and is coextensive with the flat peripheral undersurface of recess 72 of holder section 68a. A flat circular flange 86 extends all around the holder section 68b at the bottom thereof. Spaced above that flange and extending all around the section is a radially-inwardly-extending groove 88 which is arranged to cooperate with the lip 72a on section 68a to connect the two sections together.

The FIG. 5 electrode embodiment is assembled in much the same way as the other embodiments. The annular support layer 10 is positioned on flange 86 of the lower holder section 68a. Then the gel pad 16 is positioned in the recess 84 in that same section. Finally, the terminal assembly comprising the terminal strip 54 crimped to the electric lead 58 and staked to the contact member 52 is pressed into the same recess 84. This forces the gel pad 16 down through opening 82 so that its lower surface is more or less flush with the lower surface of housing section 68b. Finally, the upper housing section 68a is positioned over section 68b with its slot 76 aligned with electric lead 58 and pressed down toward section 68b whereupon its lip 72a snaps into the circular groove 88 in section 68b, thereby clamping the two sections together and capturing the support layer as well as the gel pad and terminal.

The FIG. 5 electrode has the same advantages as the others in that it is relatively inexpensive to manufacture and easily assembled by hand. During such assembly, all of its various parts are automatically positioned at the proper location relative to one another by the configuration of the holder and, when assembled, the electrode constitutes a very compact lightweight device which causes little patient discomfort. The FIG. 5 embodiment has an advantage over the others in that its terminal and electrical connection to the monitoring apparatus is completely enclosed within holder 68. Therefore, the terminal 52 cannot be contacted or disconnected intentionally or inadvertently from the monitoring apparatus by the patient.

It will be seen from the foregoing, then, that my various electrode embodiments are relatively inexpensive to manufacture as compared with prior electrodes of this general type. Yet the electrodes are lightweight and can be worn for a prolonged period with minimum discomfort. In addition, they initiate a monitor signal which is characterized by relatively high sensitivity and minimum noise.

While we have illustrated some specific embodiments of the electrode, certain changes may be made without departing from the scope of the invention as defined by the appended claims. For example, instead of using snap fastener type elements to interconnect the two holder sections, the cooperating male and female elements may be adhesively secured or welded together, although this would add somewhat to the overall cost of assembling the electrodes. Also in some applications, it may not be desirable in the FIG. 5 embodiment, to clamp the gel pad 16 to the contact member 52. In this event, the pad 16 can be retained adhesively within a recess (not shown) formed in the underside of the lower housing section, the space between the contact member 52 and pad 16 then being filled with conductive electrolyte. There also an added expense is involved. In any event, it is intended that all matter contained in the above description or shown in the accompanying drawings be interpreted as illustrative and not in a limiting sense.

It is also to be understood that the following claims are intended to cover all of the generic and specific features of the invention herein described.

What is claimed as new and desired to be secured by Letters Patent of the United States is:

1. A disposable medical electrode comprising:
   A. a holder comprising
      (1) a first generally flat holder section having
         (a) an outer surface and an inner surface,
         (b) means defining a recess in said inner surface, and
         (c) means defining a passage extending from said recess outside said first section for providing electrical access to said recess,
      (2) a second generally flat holder section having
         (a) an outer surface and an inner surface and
         (b) means defining an opening through said second section extending between said outer and inner surfaces thereof,
   B. a support layer having first and second faces engaged by said inner surfaces of said first and second holder sections, respectively, to hold said support layer in said holder, said support layer also including means defining an opening therethrough extending between said first and second faces, said second face of said support layer providing an adhesive surface,
   C. an electrical terminal disposed in said recess in said inner surface of said first holder section for electrical access thereto through said passage in said first holder section, and
   D. a gel pad having first and second opposite faces, said gel pad being disposed in registration with said opening through said support layer with said first face of said gel pad disposed in intimate contact with said electrical terminal, said inner surfaces of said first and second holder sections engaging said first and second faces, respectively, of said gel pad to hold said gel pad in position between said holder sections with said second face of said gel pad projecting through said opening in said second holder section,
   said two holder sections being secured together so as to maintain said inner surfaces thereof in engagement with said support layer and said gel pad and thereby hold them in assembly.

2. The electrode defined in claim 1 and further including means for mechanically securing the terminal within the recess in the first holder section.

3. The electrode defined in claim 2 wherein
   A. the passage from the recess in the first holder section is in the top of that section,
   B. the terminal comprises an electrically conductive snap fastener element having
      (1) a substantially flat body, and
      (2) a top projecting from the body through said passage, and
   C. the securing means comprises a lip extending around the mouth of the recess in the first holder section engaging around the terminal body to retain the terminal in the recess.

4. The electrode defined in claim 2 wherein
   A. the means defining the passage from the recess in the first holder section is located in the top of that section,
   B. the terminal comprises an electrically conductive snap fastener element having
      (1) a substantially flat body,
      (2) a top projecting from the body through the passage from the recess in the first holder section,
   C. and the securing means comprises an annular protuberance extending around the top of the terminal, and
   D. the passage from the recess in the first housing holder section is in register with the terminal top and of a size to snugly receive the top and its protuberance so that, when the top is received in the passage, it is retained there by engagement of the passage wall with the protuberance.

5. The electrode defined in claim 1 wherein the terminal comprises
   A. an electrically conductive contact member in intimate contact with the first face of the gel pad,
   B. a terminal strip
      (1) in electrical contact with the contact member,
      (2) mechanically secured thereto, and
      (3) projecting into the recess in the first holder section, and
   C. an electrical lead
      (1) in electrical contact with the terminal strip,
      (2) mechanically secured thereto, and
      (3) extending out of the first holder section through said passage therein.

6. The electrode defined in claim 5 wherein
   A. said terminal strip is staked to said contact member, and
   B. said lead is crimped to said terminal strip.

7. The electrode defined in claim 1 wherein said first and second holder sections also include
   A. a male fastener component formed on said inner surface of one of said sections, and
   B. a mating female fastener component formed on said inner surface of the other of said sections and engaging said male fastener component to secure said holder sections together.

8. The electrode defined in claim 7 wherein the male and female fastener components are continuous all around said first section recess and said second section opening.

9. The electrode defined in claim 7 wherein the male and female fastener components are discontinuous and are arrayed around the first section recess and the second section opening.

10. The electrode defined in claim 1 wherein said holder sections also include
    A. a first lateral lip extending around a perimeter of one of said holder sections, and B. a mating lateral groove formed in the other of said holder sections, said lip being pressed into said groove thereby securing said holder sections together.

11. A disposable medical electrode comprising
A. a thin compliant support layer having first and second faces and means defining an opening therethrough extending between said first and second faces, said second face providing an adhesive surface,
B. an electrically conductive terminal, said terminal including
   (1) a wafer-like body, and
   (2) a stud projecting from the body,
C. a compliant discoid gel pad having inner and outer surfaces, the diameter of the gel pad being less than the dimensions of the opening in the support layer, and
D. a holder, said holder comprising
   (1) an upper section having
      (a) an outer surface,
      (b) an inner surface,
      (c) means defining a recess in the inner surface,
      (d) means defining a passage from said recess through the outer surface of said upper section, said recess and said passage being sized so that the terminal body can seat in the recess with its stud projecting out of the upper holder section through said passage, said terminal body being disposed in said recess with said stud projecting out through said passage, and
   (2) a coextensive lower section having
      (a) an outer surface,
      (b) an inner surface, and
      (c) means defining a passage extending through said lower section between said surfaces, the diameter of said passage being less than the diameter of said gel pad, and
   (3) cooperating fastener means formed at the inner surfaces of said holder sections, each fastener means forming a closed figure whose dimensions are greater than the diameter of the gel pad but less than the dimensions of the opening in the support layer, the support layer being positioned on the lower section with the fastener means extending through the opening in said support layer, the gel pad being positioned on the lower section within the closed figure formed by said fastener means, the terminal being received in the recess in the upper holder section, the holder sections being disposed with their inner surfaces in juxtaposition, thereby sandwiching between them the inner edge margin of the support layer and the outer edge margin of the gel pad, and being secured together by the fastener means so that the inner surface of the gel pad is in intimate contact with the body of the terminal and the outer surface of the gel pad is substantially coplanar with the adhesive surface of the support layer and the outer surface of the lower holder section.

12. The electrode defined in claim 11 wherein the terminal comprises a male snap fastener element having an electrically conductive outer surface.

13. The electrode defined in claim 11 and further including cooperating means between the upper holder section and the terminal for mechanically retaining the terminal in the recess in the upper holder section.

14. A disposable medical electrode comprising
A. a flat compliant support layer having first and second faces and means defining an opening therethrough extending between said first and second faces, said second face providing an adhesive surface,
B. a compliant discoid gel pad having inner and outer surfaces and having a diameter less than the dimensions of the opening in the support layer,
C. an electrical terminal,
D. a holder for maintaining the support layer, gel pad and terminal in relative juxtaposition, said holder comprising
   (1) a first flat relatively stiff holder section having
      (a) an outer surface,
      (b) an inner surface,
      (c) a recess formed in the inner surface and
      (d) a passage extending from the recess,
   (2) a second flat relatively stiff holder section, said second holder section
      (a) being coextensive with the first section,
      (b) having an outer surface,
      (c) having an inner surface facing said inner surface of said first holder section, and
      (d) having a passage extending between its outer and inner surfaces, said passage having a diameter which is less than the diameter of the gel pad, and
   (3) cooperating means on said first and second holder sections securing said sections together, said support layer being positioned on said inner surface of said second holder section with said cooperating means extending through the opening in the support layer, at least a portion of the terminal being received in the recess in the first holder section, the two holder sections thereby clamping the terminal and the support layer between them, the gel pad being mounted in the passage in the second holder section so that its inner surface is in intimate contact with the terminal and its outer surface is substantially coplanar with the adhesive surface of the support layer and the outer surface of the second holder section, and
E. means extending from said recess through said passage to the exterior of the holder for establishing electrical contact with the terminal.

15. The electrode defined in claim 14 wherein
A. the terminal includes
   (1) a contact member having a conductive outer surface in contact with the inner surface of the gel pad, and
   (2) an electrically conductive terminal strip electrically connected to the contact member, and
B. the contact establishing means includes an electrical lead electrically connected to the terminal strip and extending from said recess to the outside of the holder.

* * * * *